(12) United States Patent
Baker et al.

(10) Patent No.: US 6,485,734 B1
(45) Date of Patent: Nov. 26, 2002

(54) TOPICAL COMPOSITION FOR THE TREATMENT OF HEAD LICE AND NITS AND METHOD

(76) Inventors: Bradley Baker, 706 Birmingham La., Monroe, NC (US) 28110; David Holland, 427 Lafayette Way, Camden, SC (US) 29020; Forrest Fesperman, 2501 Alpine Rd., Durham, NC (US) 27707

(*) Notice: Subject to any disclaimer, the term of this patent is extended or adjusted under 35 U.S.C. 154(b) by 0 days.

(21) Appl. No.: 09/287,808

(22) Filed: Apr. 7, 1999

(51) Int. Cl.⁷ .......................... A01N 25/32; A01N 65/00
(52) U.S. Cl. ........................................ 424/406; 424/767
(58) Field of Search .................. 424/405, 406, 424/195.1, 196.1, 401, 767, 774

(56) References Cited

U.S. PATENT DOCUMENTS

| 5,411,992 A | * | 5/1995 | Eini et al. .................... 514/731 |
| 5,792,467 A | * | 8/1998 | Emerson et al. ............. 424/405 |
| 5,839,224 A | * | 11/1998 | Emerson et al. ................ 47/58 |
| 5,858,383 A | * | 1/1999 | Precopio et al. ............ 424/405 |
| 6,103,248 A | * | 8/2000 | Burkhart et al. ............ 424/401 |

OTHER PUBLICATIONS

U.S.D.A. Bureau of Entomology and Plant Quarantine E-Series A77.312 751–812; Preliminary Tests of Plant Materials as Insecticies.

U.S.D.A. Dept. of Agriculture Agriculture Handbooks 144–156 (1958–1959), @ p. 165 describing Yucca(s).

* cited by examiner

Primary Examiner—Neil S. Levy
(74) Attorney, Agent, or Firm—Robert G. Rosenthal

(57) ABSTRACT

A composition is provided which serves as a pediculicide for topical application to the hair and scalp of humans and other animals. The solutions take the form of a mousse, shampoo and a detergent. The active ingredient is a saponin, preferably derived from yucca extract.

7 Claims, No Drawings

TOPICAL COMPOSITION FOR THE TREATMENT OF HEAD LICE AND NITS AND METHOD

FIELD OF THE INVENTION

This invention relates to the treatment of head lice and more particularly to saponin containing products that kill human head lice, pediculus humanus capitus, nits (lice eggs) and other types of lice, for example clothing lice, pediculus humanus humanus and other aphids.

BACKGROUND OF THE INVENTION

Head lice (pediculus humanus capitus) are tiny, wingless, flat bodied parasites that live on the human body and feed by sucking blood from the host. If not destroyed, they multiply rapidly and can spread disease. Head lice are found in both the developed and undeveloped countries of the world and they can be caught by anyone, regardless of race or socio-economic background. Head lice are generally found on the scalp and cause itchy, red spots. They leave nits or eggs which female lice attach to the base of hair shafts near the scalp. If a lice infestation is present, it is usually indicated by the presence of small, whitish flecks, securely attached to the base of the hair, especially behind the ears and on the forehead. The eggs have a gestation period on the order of one week and infestations are common in day care centers and schools as head lice usually spread by direct contact, which occurs more frequently among children.

Eradication of head lice consists of over-the-counter and prescription medications. Treatment typically involves scrubbing the infested area to loosen the lice followed by application of medication, usually a shampoo which is left on for a prescribed time. After the prescribed time has elapsed, the shampoo is rinsed off. Then, the hair is combed to remove lice. As lice have a gestation period of one week, a second application is done at that time to kill the newly hatched lice as most currently available products to not kill nits.

In view of the foregoing, it will be seen that head lice is a significant public health problem with an eye towards eradication, a number of treatment approaches have developed, namely, pyrethrins, synthetic pyrethrouds (permethrin and bioallethrin), organophosphates (Malathion or maldison), and herbal. All of the foregoing approaches have inherent drawbacks and deficiencies.

Generally, all head lice products contain insecticides and most work by attacking the nervous system of the lice and the active ingredient must have low acute toxicities for humans. Natural pyrethrins are used as pediculicdies worldwide and demonstrate a good safety level. However, although pyrethrins are the most common ingredients in anti-lice products, most of these compositions are shampoos which, due to their presentation, show minimal activity against louse eggs. Shampoos normally fail for several reasons, but most significant among these is the large dilution factor which occurs during use. Depending on how oily the hair to be treated is, the average head of hair will take between 90–150 mls of water to be throughly wetted. Even in hard water areas approximately 5 ml of shampoo is required to work up a good lather, yielding a dilution of 1:30. If the water is soft, the dilution factor could be higher than 1–150.

Many commonly used pediculicidal compositions rely on residual action on the hair by the pesticide after application of the composition to the patient. Permethrin creme rinses are applied after shampooing and rely on the residual action of the insecticide on the hair after the shampoo treatment. One of the drawbacks of Permethrin is that as residual activity wears off, there will be a point beyond which any lice invading the head will not be killed by lower insecticidal levels. Such conditions may lead to the insecticide resistance.

Turning now to the eggs, an insecticide needs to make its way through a physical system that is designed to keep out a variety of chemical materials and to keep water in. The egg shell has a detachable cap that bears a number of air pores that act effectively to exclude fluids by will allow the passage of gasses, and it is through these pores that the developing embryo breathes. However, it is also through these pores that suitable formulations can penetrate. The problems of penetration are dependent on physical parameters. Generally, the more viscous a fluid, and the greater the surface tension, the less chance of penetration of the pores. However, even alcoholic solutions, which have the advantage of a low wetting angle that should allow fluid to flow into the pores, are not free of problems because they can develop air bubbles that are larger than the pores and that subsequently hinder the penetration to the chrionic membrane of the egg.

Aqueous lotions, creme renses and shampoos have too great a wetting angle for fluid to flow into the pores directly, and will only enter if appropriate excipients are included that will wet and flow more readily than the body of the formulation. Consequently, despite the bubbles of a shampoo's foam being small enough to enter the pores, they are inhibited in an aqueous medium.

It is accordingly an object of the present invention to provide an improved treatment for eradication of head lice and nits.

It is another object of the present invention to provide an improved treatment for the eradication of head lice and nits which is safe.

It is still another object of the present invention to provide an improved treatment for the eradication of head lice and nits which effective.

It is yet another object of the present invention to provide an improved treatment for the eradication of head lice and nits which can be accomplished with one application.

It is a further object of the present invention to provide an improved treatment for the eradication of head lice and nits which is non-toxic to humans.

It is a still further object of the present invention to provide an improved treatment for the eradication of head lice and nits which is new, and therefore, not subject to resistance.

It is a still further object of the present invention to provide a preventative shampoo which when used after the initial treatment, will prevent re-infestation.

SUMMARY OF THE INVENTION

In accordance with the present invention, there is provided a method of eradicating Pediculus humanus capitis in humans comprising the steps of applying to the hair and scalp in need of such treatment, an effective amount of a solution consisting essentially of a saponin containing botanical extract, such as yucca extract, at a concentration of at least 200 ppm, based on total weight of the solution, which, for example is found in yucca juice. Thus, a formulation containing from about 40% to 60% yucca juice is effective. The solution is allowed to remain in contact with the hair and scalp for a preslected period of time. Thereafter, the solution is washed from the hair and scalp.

In one aspect of the invention, the solution takes the form of a leave-in conditioner, such as a mousse and includes a thickener, such as a carbomer. In this case the solution is maintained in contact with the hair and scalp overnight while sleeping and is shampooed out in the morning.

In another aspect of the invention, the solution takes the form of a shampoo and includes a surfactant. This shampoo may be employed to wash the conditioner out of the hair and scalp after use or may be used regularly by itself to prevent re-infestations of pediculus humanus capitus and nits.

In still another aspect of the invention, the solution takes the form of a laundry detergent which kills both pediculus humans capitus and pediculus humanus humanus and their respective nits during washing.

DETAILED DESCRIPTION OF THE PREFERRED EMBODIMENTS

While the present invention will be described more fully hereinafter, in which particular embodiments are shown, it is to be understood at the outset that persons skilled in the art may modify the invention hereindescribed while still achieving the favorable results of this invention. Accordingly, the description which follows is to be understood as a broad teaching disclosure directed to persons of skill in the appropriate art and not as limiting upon the present invention.

It will be noted at the outset that the hair and scalp referred to herein is intended to include all animals, especially house pets and humans. In addition, when Pediculus humanus capitis or Pediculus humanus humanus are referred to herein, the respective nits of each of the foregoing are to be included therein, and visa versa.

Referring now to a first preferred embodiment of the invention, there is provided a method of eradicating Pediculus humanus capitis in animals and particularly in humans which comprises the steps of applying to the hair and scalp in need of such treatment, an effective amount of a botanical extract containing solution consisting essentially of a yucca juice which contains saponin. This solution is formulated so that saponin is present at a concentration of at least 200 ppm, based on total weight of the solution (i.e., from about 40% to 60% by weight of yucca juice, as more fully explained hereinbelow). The saponin extract is selected from the group consisting of saponin containing botanicals such as yucca extract, soap nut oil and tribulus terrestris, with yucca extract being preferred. The saponin containing solution is allowed to remain in contact with the hair and scalp for a preselected period of time, which period of time is sufficient to kill the lice. In addition, in the event nits are present, the solution is allowed to remain in contact with the hair for a preselected period of time which period of time is sufficient to loosen the nits by partially dissolving the starch like substance with which the nits are attached to the hair. After the preselected period of time has elapsed, the solution is washed or shampooed from the hair by conventional means, such as with an over the counter shampoo. Thereafter, the hair and skin is combed or brushed to remove the nits. However, as will be seen hereinbelow, the effectiveness of the treatment is enhanced by employing a shampoo according to the present invention.

The active ingredient is a saponin-containing yucca juice which contains 10%–20% yucca extract (depending on a number of factors including growing conditions). The yucca extract is comprised of approximately 20% saponins. The present invention employs yucca plant extract which is effective at concentrations at or above 12.00% by weight (yielding a saponin content of 0.18%–0.30%) to kill lice and to prevent infestations from occuring. Saponins are present in many monocot families (e.g., Liliacese, Mmarylidaceae, and Dioscrocaccae) and in dicots (e.g., Scrohulariaccae, Leguminosac, and Lolanaceae). Saponins can be extracted from various parts of saponin-containing trees and plants, including the fruit, leaves, roots, bark and trunk. Saponin-containing extracts can be obtained by crushing or pressing suitable portions of the tree or plant to yield a saponing-containing juice. The liquid may be subsequently purified to remove debris. A saponin-containing extract may also be obtained through solvent etraction using solvents such s methanol, ethanol, acetone, ethylacetate, chloroform, hexane, and dichloromethaine. Further, leaves, bark and other portions of the saponin-containing materials may be ground and dried to obtain a suitable solid extract.

One preferred source of saponin-containing extract is the tree *Yucca schidrigera*. The extract can be obtained by crushing or pressing the log of the Yucca tree to yield a liquid which is referred to herein as "yucca juice". Exemplary *Yuca schidigera* extracts are available from Berghuasen Corporation, Cincinnati, Ohio as "Yucca Extract 61", and from Calgene Chemical, Inc. of Des Plains, Ill., under the trade name "Agro Y-100".

The present invention operates to eradicate lice and their nits by a substantially different mechanism that that found in the prior art. More specifically, saponin acts as the active ingredient in the solution according to the present invention and with respect to hatched lice, it acts on the cell protoplasm, a liquid crystalline structure and changes it into a solid. As a result, holes are opened in the cell walls and the cell fluids flow out of the cells, thus, killing the lice.

In addition, it will be noted that the nits are attached to the hair by means of a starch-like substance. The pediculicidal treatments according to the prior art must generally be repeated seven to ten days after the initial treatment in order to kill the newly hatched nits. In contrast, the saponin according to the present invention is effective in partially dissolving the starch by which the nits are affixed to the hair. Upon completion of treatment, the nits are easily combed out of the hair and scalp. Thus, it will be seen that the present invention is an effective pediculicide which substantially eradicates lice and their nits with only one application, as compared with at least two as required by the prior art.

In one embodiment of the invention the solution takes the form of a conditioner, an effective amount of which (approximately 1.0 fluid oz.) is applied to the hair and scalp. The conditioner is applied prior to going to bed and is washed out the next morning (i.e., remains in contact for at least 6 hours) and contains:

| Component | % w/w |
| --- | --- |
| water | from about 40–60 |
| saponin containing yucca juice | from about 40–60 |
| thickening agent | from about 1.0–2.0 |
| alkalai/acid donor | less than 2.00 |
| fragrance | less than 2.00 |
| preservative | less than 2.00 |

As used above the term "thickening agent" includes Acrylic polymers such as carbomers (i.e., CARBOBOL ULTREZ 10 Polymer available from BF Goodrich of Cleveland, Ohio).

A formulation of the present invention that was found to be an effective conditioner after remaining on the hair and scalp of the user overnight while sleeping was as follows:

| Component | % w/w |
|---|---|
| Carbomer 934 | 1.50 |
| Tea 99 | 1.80 |
| Water | 47.60 |
| Saponin containing yucca juice | 48.40 |
| Peppermint fragrance | 0.50 |
| Dowcil 200 | 0.20 |

In addition, the conditioner may be washed out of the hair with a pediculicidal shampoo which may also be periodically used to prevent infestation or re-infestation of the hair and scalp. In order to prevent re-infestation approximately 1.0 fluid oz. of the shampoo should be applied to the wet hair and scalp. The shampoo is applied in the same manner as the conditioner described hereinabove and is allowed to remain in the scalp for an preselected period of time, normally at least 20 minutes and preferred compositions according to the present invention thus contain:

| Component | % w/w |
|---|---|
| Water | from about 40–60 |
| surfactant | from about 20–50 |
| saponin containing yucca juice | from about 0.40–1.00 |
| preservative | less than 2.00 |
| fragrance | less than 2.00 |
| alkalai/acid donor | less than 2.00 |

A typical formulation of the shampoo is as follows:

| Component | % w/w |
|---|---|
| Water | 49.60 |
| Mackadet SBC-8 | 30.00 |
| Saponin containing yucca juice | 20.00 |
| Dowcil 200 | 0.10 |
| Peppermint fragrance | 0.30 |

Lastly, the present invention may also be formulated as a laundry detergent which may be used to further prevent re-infestation. When used, approximately 4.0 fluid oz. should be added to a typical wash load. Preferred compositions according to the present invention thus contain:

| Component | % w/w |
|---|---|
| Water | 20.00–40.00 |
| Surfactant | 20.00–40.00 |
| Saponin containing yucca juice | 10.00–20.00 |
| Preservative | less than 2.00 |
| Fragrance | less than 2.00 |
| Acid/alkalai donor | less than 2.00 |

A typical formulation of the laundry detergent is as follows:

| Component | % w/w |
|---|---|
| Water | 26.00 |
| Sodium salt of DDBSA | 26.00 |
| TEA | 3.00 |
| IPA | 6.00 |
| Sodium Chloride | 1.00 |
| Saponin containing yucca juice | 12.00 |
| Neodol 25-7 | 24.00 |
| DTPA 40 | 2.00 |
| Citric Acid | QS pH 8 |

In addition, conventional fragrances, preservatives, and ph adjusting compounds may be added to any of the above described formulations without adversely affecting the performance of the pediculicide.

It will be noted that the preferred saponin containing extract referred to herein is yucca extract wherein the active ingredients comprise approximately ten per cent of the extract. The saponin content is then 10% to 20% by weight of the aforementioned extract. Note also that the saponin content varies by plant species selected and is also dependent on growing conditions.

From the foregoing, it will be seen that the present invention presents a novel approach to preventing infestations of lice and nits from 6occuring in the first instance and in the event they are discovered, presents a novel single application approach to their eradication and removal.

It is understood that various modifications may be made to the invention described herein without departing from the intended scope of the invention.

That which is claimed is:

1. A method of eradicating *Pediculus humanus* capitis comprising the steps of:
    A) applying to the hair and scalp in need of such treatment, an insecticidally effective amount of a solution whose active ingredient consists of:
        i) a saponin containing botanical extract at a concentration of at least 200 ppm, based on total weight of the solution;
        ii) the solution optionally contains an acrylic polymer in a concentration from about 1.0 to about 2.0 weight per cent;
    B) allowing the solution to remain in contact with the hair and scalp for at least 20 minutes, said 20 minutes being sufficient to kill the *Pediculus humanus* capitis;
    C) washing the solution from the hair and scalp after at least 20 minutes has elapsed.

2. The method according to claim 1 wherein the solution includes the acrylic polymer.

3. The method according to claim 1 further including the step of combing/brushing the hair to remove nits which have been loosened by the application of the solution.

4. The method according to claim 1 wherein the solution is removed from the hair and scalp with a shampoo.

5. The method according to claim 1 wherein the solution is maintained in contact with the hair and scalp for at least twenty minutes.

6. A method of eradicating Pediculus humanus capitis comprising the steps of:
    A) applying to the hair and scalp in need of such treatment, an insecticidally effective amount of a conditioner whose active ingredient consists of:
        i) a saponin extract at a concentration of at least 200 ppm, based on total weight of the solution;

B) allowing the solution to remain in contact with the hair and scalp overnight while sleeping for at least six hours;

C) washing the solution from the hair and scalp.

7. The method according to claim 6 wherein the conditioner further includes the step of combing the hair and scalp; whereby the nits that have been loosened by the treatment are removed.

* * * * *